United States Patent [19]

Perricone

[11] Patent Number: 4,775,530

[45] Date of Patent: Oct. 4, 1988

[54] METHOD FOR TREATMENT AND PREVENTION OF PSEUDOFOLLICULITIS BARBAE

[76] Inventor: Nicholas V. Perricone, 18 Corbin Cir., Branford, Conn. 06450

[21] Appl. No.: 666

[22] Filed: Jan. 6, 1987

[51] Int. Cl.$^4$ .............................................. A61K 7/15
[52] U.S. Cl. ...................... 424/73; 514/557; 514/574
[58] Field of Search .............. 424/73, DIG. 5; 514/557, 574, 944, 945, 969

[56] References Cited

U.S. PATENT DOCUMENTS

| | | | |
|---|---|---|---|
| 3,920,835 | 11/1975 | Van Scott et al. | 514/546 X |
| 4,105,782 | 8/1978 | Yu et al. | 514/574 X |
| 4,143,160 | 3/1979 | Osberghaus et al. | 424/73 X |
| 4,197,316 | 4/1980 | Yu et al. | 514/459 X |
| 4,228,163 | 10/1980 | Bliss | 514/171 |
| 4,234,599 | 11/1980 | Van Scott et al. | 514/451 |
| 4,363,815 | 12/1982 | Yu et al. | 424/DIG. 4 |
| 4,380,549 | 4/1983 | Van Scott et al. | 514/23 |
| 4,525,344 | 6/1985 | Tutsky | 424/73 |

*Primary Examiner*—John E. Kittle
*Assistant Examiner*—Susan S. Rucker
*Attorney, Agent, or Firm*—St. Onge Steward Johnston & Reens

[57] ABSTRACT

Treatment and prevention of pseudofolliculitis barbae ("razor bumps") is effected by topical application to beard areas of an alpha-hydroxy acid or derivative thereof, most preferably glycolic acid or glycolic acid derivatives, and most preferably as a component of a cosmetically acceptable lotion, cream, ointment, soap, shaving foam, stick, gel or solution.

18 Claims, No Drawings

METHOD FOR TREATMENT AND PREVENTION OF PSEUDOFOLLICULITIS BARBAE

BACKGROUND OF THE INVENTION

The present invention relates to the disorder known as pseudofolliculitis barbae, and more particularly to a method and topical preparation for treatment and prevention of pseudofolliculitis barbae.

Pseudofolliculitis barbae is the clinical name given to the condition commonly referred to as "razor bumps". Generally, the condition describes the ingrowth of emerged facial hairs back into the skin at a location closely adjacent to the follicle from which the hair emerged. This penetration back into the skin causes an antigenic, foreign-body reaction at the point of penetration, resulting in lesions consisting of firm papules and pustules in which the ingrowing hair can become buried. Additional infections can become superimposed on this basic state, augmenting the inflammatory reaction. As a consequence, shaving becomes problematic and painful.

From a purely mechanical point of view, pseudofolliculitis barbae comes about by virtue of strongly curved facial hairs. For this reason, the condition tends to have a greater incidence in males of the Negro race. These curved facial hairs emerge closely parallel to the skin and, owing to their curvature, are biased toward reentry into the skin. Because of their emergence so close to the skin surface, these hairs often are not closely cut at their point of emergence during shaving. Indeed, shaving exacerbates the condition (and to a large degree is the sine qua non for it) because shaving serves to obliquely cut these hairs, above the skin surface, leaving relatively sharp pointed tips which facilitate skin penetration. Before the next shaving, the point hair ingrows into the skin, bringing about the reactions and conditions earlier discussed.

Suggestions for dealing with pseudofolliculitis barbae involve both treatment and prevention. In terms of a dealing with a pre-existing condition, it is necessary to treat the lesions and any associated secondary infections, and for this reason various therapeutic agents and antibiotics have been suggested. With these effects of the condition in check, abstinence from shaving will generally take care of the condition itself because the continued growth of the curved hairs eventually results in a spring-like action which will pull the ingrown tip out of the skin. Obviously, however, total abstinence from shaving and/or repeated cycles of occurrence and treatment of the condition are not highly practical.

Prevention of pseudofolliculitis barbae per se has proven difficult. In theory at least, frequent shaving which cuts emergent facial hairs right at the skin surface could eliminate the condition by regularly removing hairs before they have had an opportunity to grow and reenter the skin. This theoretical solution has, however, proven to be highly impractical. In the first place, cutting facial hairs right at the skin level is difficult and, since frequent shaving concomitantly brings about frequent provision of sharp hair ends, onset of the condition actually is hastened. Further, efforts to cut facial hairs right at the skin level often involve a stretching of the skin which actually results in cutting of the hairs below the skin level. This can result in an intra-follicular ingrown hair wherein the sharp-tipped curved hair, instead of emerging from the follicle, penetrates the follicular wall and brings about the same or similar foreign body reactions as occur when a hair properly emerges from its follicle but then reenters the skin.

The use of dipilatory compositions has been suggested for prevention of pseudofolliculitis barbae, and can be effective in achieving the non-cutting removal of hairs before they can reenter the skin. Also suggested have been compositions which soften the facial hairs so as to inhibit their ability to penetrate the skin. However, most of the compositions suggested are such as to bring about skin irritation or other side effects when used in the frequency required to insure prevention of the condition.

On the general subject of pseudofolliculitis barbae, reference can be had to Strauss et al., "Pseudofolliculitis Of The Beard," A.M.A. Archives of Dermatology, and U.S. Pat. Nos. 4,525,344; 4,228,163; and 3,981,681.

SUMMARY OF THE INVENTION

It is an object of the present invention to provide a method for treating and preventing, or at the least for minimizing the occurrence and severity of, pseudofolliculitis barbae.

Another object of the invention is to provide a method for treating and preventing pseudofolliculitis barbae, which method is essentially devoid of harmful or uncomfortable side effects.

Yet another object of the invention is to provide agents and compositions for topical application to the facial area, either before, incident to or after shaving, so as to substantially prevent occurrence of pseudofolliculitis barbae.

Still another object of the invention is to provide topical agents and compositions for treatment and prevention of pseudofolliculitis barbae which may be employed without bringing about skin irritation or harmful side effects.

These and other objects are achieved by virtue of the discovery that topical application to facial beard areas of alpha-hydroxy acids or derivatives thereof is effective in preventing or minimizing the occurrence of pseudofolliculitis barbae and in alleviating such condition where it is pre-existing.

The alpha-hydroxy acids or derivative compounds may conveniently be employed in the form of solution, gel, powder, stick, lotion, cream, soap, shaving foam or ointment utilizing cosmetically acceptable ingredients, and in such forms can be safely employed by the user in a regular regimen either before, incident to or after shaving.

Based upon testing to date, the preferred topical agent for use in the present invention is the alpha-hydroxy acid glycolic acid, and its pharmaceutically acceptable metal or ammonium salts, esters, anhydrides, lactones and amides.

DETAILED DESCRIPTION OF THE INVENTION

As used herein, the terminology "alpha-hydroxy acid" has reference to and encompasses the general class of organic compounds containing at least on hydroxyl group and at least one carboxyl group, and wherein at least one hydroxyl group is located on the alpha-carbon atom. Typically, the compounds so defined will have a single hydroxyl group (other than that associated with a carboxyl moiety), on the alpha-carbon atom, and may contain one, two or three carboxyl groups. Most typically, these compounds will have a basic structure of lower aliphatic compounds having from two to six carbon atoms.

The "derivatives" of these alpha-hydroxy acids most typically will involve derivatives related to the carboxyl functionality, i.e., wherein the hydrogen or hydroxyl portion of the carboxyl moiety is substituted by metallic ions (to form salts), alkoxy groupings (to form esters), ammonium ions (to form ammonium salts), as well as other substitution reactions and products leading to formation of corresponding lactones, anhydrides or amides. However, the derivatives may also include reactions involving the alpha-hydroxyl group, most notably ketone formation, to form corresponding alpha-keto carboxylic acids.

Among the hydroxy acids and derivative compounds useful in the present invention for treating and preventing pseudofolliculitis barbae are the hydroxy monocarboxylic acids, such as glycolic acid, glucuronic acid, galacturonic acid, gluconic acid, glucoheptonic acid, α-hydroxybutyric acid, α-hydroxyisobutyric acid, α-hydroxyisocaproic acid, α-hydroxyisovaleric acid; and the di- and tricarboxylic hydroxy acids, such as malic acid, muric acid, citric acid, saccharic acid, tartaric acid, tartronic acid, isocitric acid, dihydroxymaleic acid, dihydroxytartaric acid, and dihydroxyfumaric acid. Derivatives involving keto groups include keto acids and keto esters such as pyruvic acid, methyl pyruvate, ethyl pyruvate, isopropyl pyruvate, benzoylformic acid, methyl benzoylformate, and ethyl benzoylformate.

The hydroxy acids and related compounds may be employed in free acid form, as esters, lactones, amides, anhydrides, inorganic metal salts or ammonium salts. By virtue of the slightly acidic nature of the human skin, certain salts of these acids may convert, at least partially, to free acid form upon use.

In the preferred form of the invention, the active hydroxy acid or related compound will be used as an ingredient in a cosmetically acceptable gel, soap, shaving foam, lotion, ointment, solution, cream or the like in order to achieve more uniform distribution of the active ingredient on the facial areas, minimize excess use of the active ingredient, maintain concentrations at levels which will not bring about skin irritation, and to take advantage of other ingredients in the composition (e.g., lanolin, stearates, etc.). In such ointments, solutions or the like, the active ingredient generally will be present in the range of from about 2 to 20% by weight, most preferably from about 3 to 7% by weight, and still more preferred, about 5% by weight, particularly for glycolic acid and its derivatives. Generally, the pH of any such preparation will be between about 2.0 and 4.0 for most preferred use, and may include various compounds or buffering agents to achieve and/or maintain this pH.

Irrespective of the composition by which the active alpha-hydroxy acid or derivative is topically applied to beard areas, the topical application can be effected regularly (e.g., once or twice daily) before or after shaving (preferably before) or incident to shaving (e.g., as part of a shaving cream formulation).

The mode by which the alpha-hydroxy acids and derivatives are effective in treatment and prevention of pseudofolliculitis barbae as described herein is not particularly well understood, but may be related to the reducing properties of the active compounds and/or their interference with chemical reactions, whereby the normal formation of disulfide bonds in the hair shaft is prevented or minimized, permitting hairs to grow straighter. It also should be noted that alpha-hydroxy acids and certain derivatives thereof have in the past been taught as means for preventing disorders of hyperkeratinization (as well as for other uses related to skin problems). See, for example, U.S. Pat. Nos. 4,105,782; 4,380,549; 3,920,835; 4,197,316; 4,363,815; 4,105,783; and 4,234,599. While pseudofolliculitis barbae may have associated with it a component of hyperkeratosis, it is, if present, quite minimal as compared to other causes and effects of the condition, and accordingly the activity and effectiveness of the alpha-hydroxy acids and derivatives in the present invention is not apparently related to effectiveness in treating hyperkeratinization disorders.

The invention is further described and illustrated with reference to the following example of a test conducted to evaluate the effectiveness of glycolic acid in treating and preventing pseudofolliculitis barbae.

For use in the test a composition was prepared in which glycolic acid was admixed with a cosmetically acceptable lotion to provide a preparation containing 5% glycolic acid (active). The components of the preparation included water, glycolic acid, cetyl alcohol, glyceryl stearate, polyethylene glycol stearates, $C_{12}$–$C_{15}$ alcohols benzoate, mineral oil, magnesium aluminum silicate, acetylated lanolin alcohol, ammonium hydroxide, xanthan gum, methylparaben and propylparaben.

The test subjects were twenty (20) black men with pre-existing conditions of pseudofolliculitis barbae rated by dermatologists as moderate to severe using accepted rating criteria. In an initial visit, histories of the subjects were taken and facial areas photographed. Most subjects indicated that daily shaving was impossible and shaved at most twice a week.

The subjects were instructed to apply the lotion to the beard area twice per day, once being right after shaving if the subject shaved that day. Follow up visits were conducted after two, four and six weeks, at which beard areas were re-photographed and the subjects asked to report satisfaction, change in shaving habits, etc.

At the follow up visits, observation by dermatologists rated an overall clinical improvement of 50% in terms of reduction of papules and pustules, confirmed by the photographic comparisons. The subjects all reported being able to shave with a safety razor with comfort on a daily basis by the two-week follow up, a condition which remained through and up to the last follow up at six weeks. No adverse side effects or skin irritation was reported or observed.

The method and preparation of the present invention may be used, then, in the treatment (i.e., alleviation of conditions and effects of) pseudofolliculitis barbae, and may then be employed in the prevention or at the least minimization of reoccurrence of the condition, as evidenced by the foregoing tests.

The foregoing description is given for purposes of describing the invention and particular embodiments thereof, but is not otherwise intended to be limiting of the variations and other embodiments encompassed within its scope, as defined by the appended claims.

What is claimed is:

1. A method for treating a subject having a pre-existing condition of pseudofolliculitis barbae and/or for substantially preventing the occurrence or reoccurrence of such condition in subjects who have exhibited such condition or who are prone to such condition, comprising topically applying to beard areas of said subject, in an amount effective to reduce pre-existing pseudofolliculitis facial lesions and/or effective to substantially prevent ingrowth of emerged facial hairs, an active compound selected from the group consisting of (a) alpha-hydroxy acids; (b) derivatives of alpha-hydroxy acids effective to treat and/or prevent pseudofolliculitis barbae; and (c) mixtures thereof.

2. The method according to claim 1 wherein said active compound is a component of a cosmetically acceptable topical preparation selected from the group consisting of gel, soap, shaving foam, solution, cream, ointment, lotion and stick.

3. The method according to claim 1 wherein said active compound is a component of a shaving composition.

4. The method according to claim 1 wherein said alpha-hydroxy acid is a lower aliphatic hydroxy acid containing a hydroxyl group on the alpha-carbon atom.

5. The method according to claim 4 wherein said alpha-hydroxy acid contains a single hydroxyl group other than that associated with the carboxyl moiety.

6. The method according to claim 5 wherein said alpha-hydroxy acid is a monocarboxylic acid.

7. The method according to claim 1 wherein said derivative of said alpha-hydroxy acid is selected from the group consisting of esters, amides, lactones, anhydrides, inorganic metal salts and ammonium salts.

8. A method for treating a subject having a pre-existing condition of pseudofolliculitis barbae and/or for substantially preventing the occurrence or reoccurrence of such condition in subjects who have exhibited such condition or who are prone to such condition, comprising topically applying to beard areas of said subject, in an amount effective to reduce pre-existing pseudofolliculitis facial lesions and/or effective to substantially prevent ingrowth of emerged facial hairs, an active compound selected from the group consisting of (a) glycolic acid; (b) a derivative of glycolic acid selected from the group consisting of esters, amides, lactones, anhydrides, inorganic metal salts and ammonium salts; and (c) mixtures thereof.

9. The method according to claim 8 wherein said glycolic acid or derivative thereof is a component of a cosmetically acceptable topical preparation selected from the group consisting of gel, soap, shaving foam, solution, cream, lotion, ointment and stick.

10. The method according to claim 8 wherein said glycolic acid or derivative thereof is a component of a shaving preparation.

11. The method according to claims 9 or 10 wherein said glycolic acid or derivative thereof comprises from about 2 to 20% by weight of said preparation.

12. The method according to claims 9 or 10 wherein said glycolic acid or derivative thereof comprises from about 3 to 7% by weight of said preparation.

13. The method according to claim 9 or 10 wherein the pH of said preparation is in the range of from about 2.0 to about 4.0.

14. The method according to claims 8, 9 or 10 wherein said active compound consists of glycolic acid.

15. The method according to claims 8, 9 or 10 wherein said active compound consists of an inorganic metal or ammonium salt of glycolic acid.

16. A method for treating a subject having a pre-existing condition of pseudofolliculitis barbae and/or for substantially preventing the occurrence or reoccurrence of such condition in subjects who have exhibited such condition or who are prone to such condition, comprising topically applying to beard areas of the subject an effective amount of an active compound selected from the group consisting of (a) alpha-hydroxy acids; (b) derivatives of alpha-hydroxy acids selected from the group consisting of esters, amides, lactones, anhydrides, inorganic metal salts and ammonium salts; and (c) mixtures thereof.

17. The method according to claim 16 wherein said active compound is topically applied in association with a cosmetically acceptable topical preparation selected from the group consisting of gel, soap, shaving foam, solution, cream, ointment, lotion and stick.

18. The method according to claim 16 wherein said active compound is topically applied in association with a shaving preparation.

* * * * *